United States Patent
Khaleghimeybodi et al.

(10) Patent No.: US 11,234,070 B2
(45) Date of Patent: Jan. 25, 2022

(54) MANUFACTURING A CARTILAGE CONDUCTION AUDIO DEVICE

(71) Applicant: Facebook Technologies, LLC, Menlo Park, CA (US)

(72) Inventors: Morteza Khaleghimeybodi, Bothell, WA (US); Antonio John Miller, Woodinville, WA (US); Ravish Mehra, Tacoma, WA (US)

(73) Assignee: Facebook Technologies, LLC, Menlo Park, CA (US)

(*) Notice: Subject to any disclaimer, the term of this patent is extended or adjusted under 35 U.S.C. 154(b) by 18 days.

(21) Appl. No.: 16/742,711

(22) Filed: Jan. 14, 2020

(65) Prior Publication Data

US 2020/0154195 A1 May 14, 2020

Related U.S. Application Data

(63) Continuation of application No. 15/993,456, filed on May 30, 2018, now Pat. No. 10,602,258.

(51) Int. Cl.
*H04R 1/10* (2006.01)
*G06F 30/00* (2020.01)
(Continued)

(52) U.S. Cl.
CPC ........... *H04R 1/1058* (2013.01); *G06F 30/00* (2020.01); *A61F 11/06* (2013.01); *B29C 33/3835* (2013.01);
(Continued)

(58) Field of Classification Search
CPC .... H04R 1/1058; H04R 25/606; H04R 25/65; H04R 25/658; H04R 2460/13;
(Continued)

(56) References Cited

U.S. PATENT DOCUMENTS 2,596,351 A 5/1952 Weaver
6,920,414 B2 7/2005 Tøpholm
(Continued)

FOREIGN PATENT DOCUMENTS

DE 102006007032 A1 8/2007
JP 2016134843 A * 7/2016 ............. H04R 25/00
(Continued)

OTHER PUBLICATIONS

Jarng, S.S. et al., "Directivity Pattern Optimization of Digital Hearing Aid by Boundary Element Method," Proceedings of the ICAD 2004, The Third International Conference on Axiomatic Design, Jun. 21-24, 2004, pp. 1-8.
(Continued)

*Primary Examiner* — Oyesola C Ojo
(74) *Attorney, Agent, or Firm* — Fenwick & West LLP

(57) ABSTRACT

A method for manufacturing a cartilage conduction audio device is disclosed. A manufacturing system receives data describing a three-dimensional shape of an ear (e.g., the outer ear, behind the ear, the concha bowel, etc.) of a user. The system identifies one or more locations for one or more transducers along a back of an auricle of the ear for the user that vibrate the auricle over a frequency range causing the auricle to create an acoustic pressure wave at an entrance of the ear canal. The system then generates a design for a cartilage conduction audio device for the user based on the one or more identified locations of the transducers at which acoustic pressure waves generated by the one or more transducers satisfy a threshold performance metric for the user. The design may then be used to fabricate the cartilage conduction audio device.

20 Claims, 6 Drawing Sheets

(51) Int. Cl.
*H04R 25/00* (2006.01)
*A61F 11/06* (2006.01)
*B29C 33/38* (2006.01)

(52) U.S. Cl.
CPC ............ *H04R 25/606* (2013.01); *H04R 25/65* (2013.01); *H04R 25/658* (2013.01); *H04R 2460/13* (2013.01)

(58) Field of Classification Search
CPC ........ H04R 2201/103; H04R 2201/107; H04R 1/1041; G06F 30/00; A61F 11/06; B29C 33/3835
See application file for complete search history.

(56) References Cited

U.S. PATENT DOCUMENTS

| | | | | |
|---|---|---|---|---|
| 7,162,323 | B2* | 1/2007 | Brumback | H04R 25/658 |
| | | | | 700/118 |
| 7,447,556 | B2* | 11/2008 | McBagonluri | H04R 25/552 |
| | | | | 700/98 |
| 8,032,337 | B2* | 10/2011 | Deichmann | H04R 1/1016 |
| | | | | 703/1 |
| 8,285,408 | B2* | 10/2012 | Schiller | G06F 30/00 |
| | | | | 700/98 |
| 9,722,562 | B1 | 8/2017 | Seguin | |
| 9,766,481 | B1 | 9/2017 | Asfaw et al. | |
| 10,335,084 | B2 | 7/2019 | Inagaki et al. | |
| 2002/0039427 | A1 | 4/2002 | Whitwell et al. | |
| 2002/0138237 | A1* | 9/2002 | Topholm | H04R 25/658 |
| | | | | 703/1 |
| 2005/0247515 | A1 | 11/2005 | Berg | |
| 2006/0115105 | A1* | 6/2006 | Brumback | H04R 25/658 |
| | | | | 381/328 |
| 2007/0025574 | A1 | 2/2007 | Azima et al. | |
| 2007/0280053 | A1 | 12/2007 | Polany et al. | |
| 2008/0232618 | A1* | 9/2008 | Johannesson | H04R 25/658 |
| | | | | 381/312 |
| 2008/0264429 | A1 | 10/2008 | Leong et al. | |
| 2009/0041287 | A1 | 2/2009 | Quinlisk | |
| 2009/0252362 | A1 | 10/2009 | Ooi et al. | |
| 2013/0136279 | A1 | 5/2013 | Brown et al. | |
| 2013/0182882 | A1* | 7/2013 | Hart | G01B 11/00 |
| | | | | 381/380 |
| 2013/0342806 | A1* | 12/2013 | Sathe | G02C 11/10 |
| | | | | 351/158 |
| 2015/0073262 | A1* | 3/2015 | Roth | A61B 5/055 |
| | | | | 600/411 |
| 2015/0141879 | A1 | 6/2015 | Harper et al. | |
| 2015/0181338 | A1 | 6/2015 | Hosoi et al. | |
| 2015/0268673 | A1 | 9/2015 | Farzbod et al. | |
| 2015/0382123 | A1* | 12/2015 | Jobani | H04R 1/1058 |
| | | | | 700/98 |
| 2016/0066851 | A1 | 3/2016 | Inagaki et al. | |
| 2016/0088409 | A1 | 3/2016 | Inagaki | |
| 2016/0088410 | A1* | 3/2016 | Chan | A61B 6/032 |
| | | | | 382/131 |
| 2016/0330546 | A1 | 11/2016 | Barrentine et al. | |
| 2017/0257710 | A1 | 9/2017 | Parker | |
| 2019/0052949 | A1 | 2/2019 | Igarashi et al. | |
| 2019/0253783 | A1* | 8/2019 | O'Callaghan | H04R 1/1083 |

FOREIGN PATENT DOCUMENTS

| | | |
|---|---|---|
| JP | 2016134843 A | 7/2016 |
| WO | WO 2008/145949 A1 | 12/2008 |
| WO | WO 2016/145261 A1 | 9/2016 |
| WO | WO 2018/093733 A1 | 5/2018 |

OTHER PUBLICATIONS

PCT International Search Report and Written Opinion, PCT Application No. PCT/US2019/027385, dated Jun. 14, 2019, 24 pages.

* cited by examiner

100

```
┌─────────────────────────────────────────────────────────┐
│ Obtain data describing a shape of an ear of a user,     │
│ the shape including an external rear portion of the ear │
│                          110                             │
└─────────────────────────────────────────────────────────┘
                             │
                             ▼
┌─────────────────────────────────────────────────────────┐
│ Position an acoustic sensor configured to detect        │
│ acoustic pressure waves from one or more transducers    │
│ of the audio device adjacent an entrance of the ear     │
│                          120                             │
└─────────────────────────────────────────────────────────┘
                             │
                             ▼
┌─────────────────────────────────────────────────────────┐
│ Identify optimal locations for each of the one or more  │
│ transducers of the cartilage conduction hearing device  │
│ that optimize the acoustic pressure waves               │
│                          130                             │
└─────────────────────────────────────────────────────────┘
                             │
                             ▼
┌─────────────────────────────────────────────────────────┐
│ Generate a device body customized for the user based on │
│ rear ear geometry of the user that conforms to the      │
│ surface of the external rear portion of the ear         │
│                          140                             │
└─────────────────────────────────────────────────────────┘
                             │
                             ▼
┌─────────────────────────────────────────────────────────┐
│ Provide a transducer in the device body for each        │
│ transducer at each of the identified optimal locations  │
│                          150                             │
└─────────────────────────────────────────────────────────┘
```

FIG. 1

MANUFACTURING A CARTILAGE CONDUCTION AUDIO DEVICE

CROSS REFERENCE TO RELATED APPLICATIONS

This application is a continuation of co-pending U.S. application Ser. No. 15/993,456, filed May 30, 2018, which is incorporated by reference in its entirety.

BACKGROUND

This disclosure relates generally to an audio device, and specifically relates to a process for manufacturing a cartilage conduction audio device.

Head-mounted displays in virtual reality (VR), augmented reality (AR), and/or mixed reality (MR) systems often include features such as speakers or personal audio devices to provide sound to users. These speakers or personal audio devices are typically formed over the ear and cover the ear (e.g., headphones), or placed in the ear (e.g., in-ear headphones or earbuds). However, a user wearing a head-mounted display in a VR, AR, and MR system can benefit from keeping the ear canal open and not covered by an audio device. For example, the user can have a more immersive and safer experience and receive spatial cues from ambient sound when the ear is unobstructed.

Moreover, like a human fingerprint that is unique to each individual, the shape of the ear (e.g., outer ear including pinna, behind the ear, concha bowl, etc.) is also unique and it is desirable for an audio device of the eyewear device to be lightweight, ergonomic, low in power consumption, and to not produce crosstalk between the ears. Such features are challenging to incorporate in a full frequency (20 Hz to 20,000 Hz) audio reproduction system while leaving the ear canal open for ambient sound from the user's environment.

SUMMARY

A method for manufacturing a cartilage conduction audio device is disclosed. A manufacturing system receives data describing a three-dimensional (3D) shape of an ear (e.g., the outer ear, behind the ear, the concha bowel, etc.) of a user. The system identifies locations (e.g., using machine learning, etc.) for one or more transducers along an external rear portion of the ear (e.g., the auricle) or along the user's tragus (on tragal cartilage). In one embodiment, identifying the location of the one or more transducers includes positioning an acoustic sensor (e.g., a microphone) adjacent a location corresponding to an entrance of the ear or ear canal to detect acoustic pressure waves from one or more transducers. The one or more transducers vibrate the external rear portion of the ear to cause the external rear portion of the ear to create an acoustic pressure wave. The locations for the one or more transducers satisfy a threshold performance metric (e.g., optimize the acoustic pressure wave at the entrance of the ear of the user) for the shape of the ear of the user. The external rear portion of the ear of the user is, thus, used as a speaker, allowing the ear canal to remain open so that the user may continue to receive sounds from the ambient environment.

The system generates a design for a cartilage conduction audio device using the shape of the ear of the user along with the identified locations for the transducers. The design may then be used to fabricate a device body for the cartilage conduction audio device that conforms to the external rear portion of the ear while housing the one or more transducers and an acoustic sensor for voice communication and recognition. Accordingly, the audio device may be incorporated into a head mounted display (HMD) for virtual reality (VR) applications, a near eye display (NED) for augmented reality (AR) applications, or as a stand-alone hearing device for listening to music, engaging in hands-free operations in conjunction with other devices (e.g., smartphones, tablet computers, video game consoles, etc.), and other activities.

BRIEF DESCRIPTION OF THE DRAWINGS

FIG. 1 is a flowchart illustrating a process of manufacturing a cartilage conduction audio device, in accordance with an embodiment.

Figure 2:
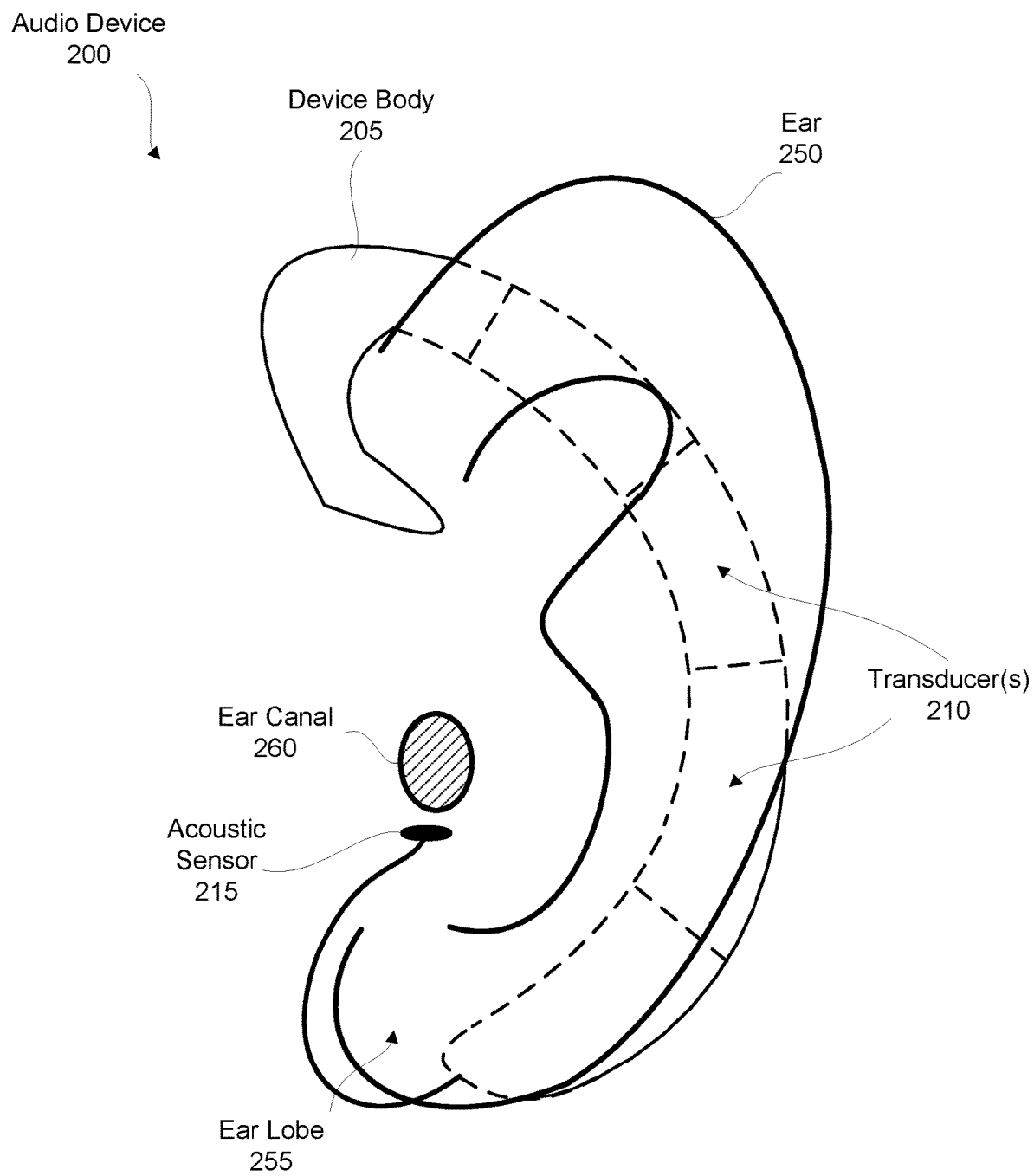
FIG. 2 is an example cartilage conduction audio device including multiple transducer along an external rear portion of the user, in accordance with an embodiment.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Overview

A method for manufacturing a custom-made cartilage conduction audio device (audio device) is disclosed that uses cartilage conduction to provide sound to an ear of a user. The audio device includes one or more transducers coupled to an external rear portion or back of the ear of the user that allows the ear canal of the user to remain unobstructed and open to ambient sound from the user's environment. Each transducer generates sound by vibrating the back of the ear (e.g., auricle, or may also be referred to as a pinna) of the user, which vibrates the cartilage of the ear of the user to generate acoustic waves corresponding to received audio content. Alternatively, or in addition to one or more transducers positioned against the back of the ear, the audio device may include a transducer positioned to vibrate the tragus of the ear.

Advantages of a cartilage conduction audio device include a reduction in crosstalk between the ears, a reduction in size and power consumption of the audio device, less sound leakage (that helps realization of private audio), and improved ergonomics. Moreover, in one embodiment, the method of manufacturing the audio device includes obtaining the shape of the user's ear in order to produce a device body of the audio device that is custom fit to the user. This allows the audio device to uses less coupling force (e.g., less static constant force on the skin) for producing a similar hearing sensation relative to an audio device that uses bone conduction, for example. This, along with the customize fit of the device conforming the shape of the user's ear, results in improved comfort for a wearable audio device, which is particularly desirable for a wearable device in which it might be desirable to wear all day.

Manufacturing a Cartilage Conduction Audio Device

FIG. 1 is a flowchart illustrating a process of manufacturing an audio device that uses cartilage conduction, in accordance with an embodiment. The process 100 may be performed by a single manufacturing system or two other entities may perform some or all of the steps of the process in other embodiments. Likewise, embodiments may include different and/or additional steps, or perform the steps in different orders.

To provide a lightweight and ergonomic audio device that conforms to the ear of the user, a manufacturing system obtains 110 data describing the shape of the ear of the user. This includes, for example, receiving data describing a three-dimensional (3D) shape of the ear (e.g., the outer ear, an external portion behind the ear, the concha bowel, etc.) of a user. Different methods can be used to obtain the 3D shape of the ear including conventional impression-based and/or stereo-based techniques. In one embodiment, a silicone with an appropriate shore-A hardness can be used to take an impression of the user's ear. Such a material would minimize distortion of the ear geometry caused from pressure applied by taking or obtaining the impression. In another embodiment, a 3D reconstruction method that captures 3D images of the ear can also be used to generate a digital model of the ear. The data for the 3D shape of the ear is then is used to customize the shape of the audio device to smoothly and comfortably conform to the user's ear.

FIG. 2 is an example cartilage conduction audio device 200, in one embodiment. Audio device 200 includes a device body 205, one or more transducer(s) 210, and an acoustic sensor 215, such as a microphone. The audio device 200 wraps around an ear 250 including the ear lobe 255 of a user while conforming to the external rear portion or auricle of the ear 250. Each transducer 210 create a pressure wave through cartilage vibration, which is used to deliver the sound to an ear canal 260 of the ear 250. The sound quality is affected by the location, position, and/or direction of the force from each transducer 210 relative to each other and also relative to the user's ear and the ear canal 360. Thus, in order to optimize sound delivery to the ear canal 360, in one embodiment, the manufacturing system positions 120 the acoustic sensor 215 adjacent a location corresponding to an entrance of the ear canal 360, as shown in FIG. 2. The acoustic sensor 215 is configured to detect the acoustic pressure waves created from the vibration of the transducers 210. The external rear portion of the ear 250 is, thus, used as a speaker, allowing the ear canal 260 to remain open to sound from the ambient environment. This is particularly advantageous in an AR system.

Using feedback from the acoustic sensor 215, the system identifies 130 locations for the one or more transducers 210 along the external rear portion of the ear 250. The individual pressure waves generated by each transducer 210 constructively and destructively interact resulting in areas of pressure wave minima and maxima. One goal of this process is to, therefore, position the one or more transducers 210 given the user's unique ear shape such that the pressure waves of the transducer 210 for audio device 200 constructively interfere at the entrance of the ear canal 260. Since the shape of the ear 250 is unique for each user, the relative locations of each transducer 210 could theoretically be different for each user. Thus, the locations for the one or more transducers 210 are chosen to satisfy a threshold performance metric. In one embodiment, the threshold performance metric corresponds to an optimal configuration of the one or more transducers 210 constrained by the possible locations of the transducers 210 in view of the user's unique ear 250 shape. The optimal configuration may coincide with a pressure wave maxima at the entrance of the ear for the given shape of a user's ear or it can be a configuration that produces a pressure wave as close as possible to the maxima in view of location constrains imposed by the shape of the ear 250. In another embodiment, the threshold performance metric is a predetermined percentage (e.g., 75%, 85%, etc.) of a predetermined pressure wave magnitude at the entrance of the ear 250 that is constant across all users in order to achieve a predefined sound quality standard. Moreover, the relative pitch, roll, and yaw of each transducer 210, as positioned in the device body 205, will also affect the location of intersection of each pressure wave, which may be relevant for some ear geometries.

While the acoustic sensor 215 could be limited to a preprocessing or training role, the acoustic sensor 215 could be a permanent feature of the audio device 200. In one embodiment, the acoustic sensor 215 includes one or more microphones placed in the device body 205 to provide real-time sound pressure wave feedback and also for speech recognition and communication purposes. For example, the acoustic sensor 215 could relay voice commands via Bluetooth to other devices. Additionally, the audio device 200 could also operate as a hands-free ear piece for making phone calls and the acoustic sensor 215 would operate as the phone receiver or microphone.

The identification 130 can be performed iteratively by physically moving the location of each transducer 210 and comparing the resulting pressure wave minima and maxima results from the acoustic sensor 215 to determine a particular arrangement for the user that creates a maxima at the entrance of the ear canal 260. In another embodiment, a model is generated using experimental and mathematical modeling (e.g., Finite Element Modeling), that can vary the location of the transducer 210 and then for each transducer 210 location, obtain their corresponding sound pressure outputs. In another embodiment, Artificial Intelligence (AI) and Machine Learning (ML) algorithms may be used to define the proper location and direction of each transducer.

Accordingly, the system generates 140 the device body 205 for the cartilage conduction audio device 200 using the shape of the ear 250 of the user along with the identified locations for each of the one or more transducers 210 and the system provides 150 the transducers 210 into the corresponding locations within the device body 205, such as by inserting each transducer 210 into the device body 205. In one example, the device body 205 is generated using a silicon or rubber-based material that conforms to the external rear surface of the ear 250.

Moreover, the head-related transfer function (HRTF) filters for the user can also be calculated using the geometry of the pinna (behind the ear, concha, tragus and anti-tragus, etc.), which are captured in 110. This can be important, since it will enable the user to have their own individualized HRTF which can greatly enhance the spatial 3D sound delivery in Virtual and Augmented Reality applications. Accordingly, the calculated HRTF filters can then be encoded with the audio signal to improve the 3D spatial sound delivery of the audio device 200. Further, given a device that conforms and fits comfortably against the skin of the user, one or more body temperature sensors can be included within the device body 205 behind the ear for health, exercise, and readiness related analysis. The user's body temperature can be monitored remotely through Bluetooth or other wireless communication protocols, and can be stored and/or monitored using a smart phone application, for example.

Figure 3:
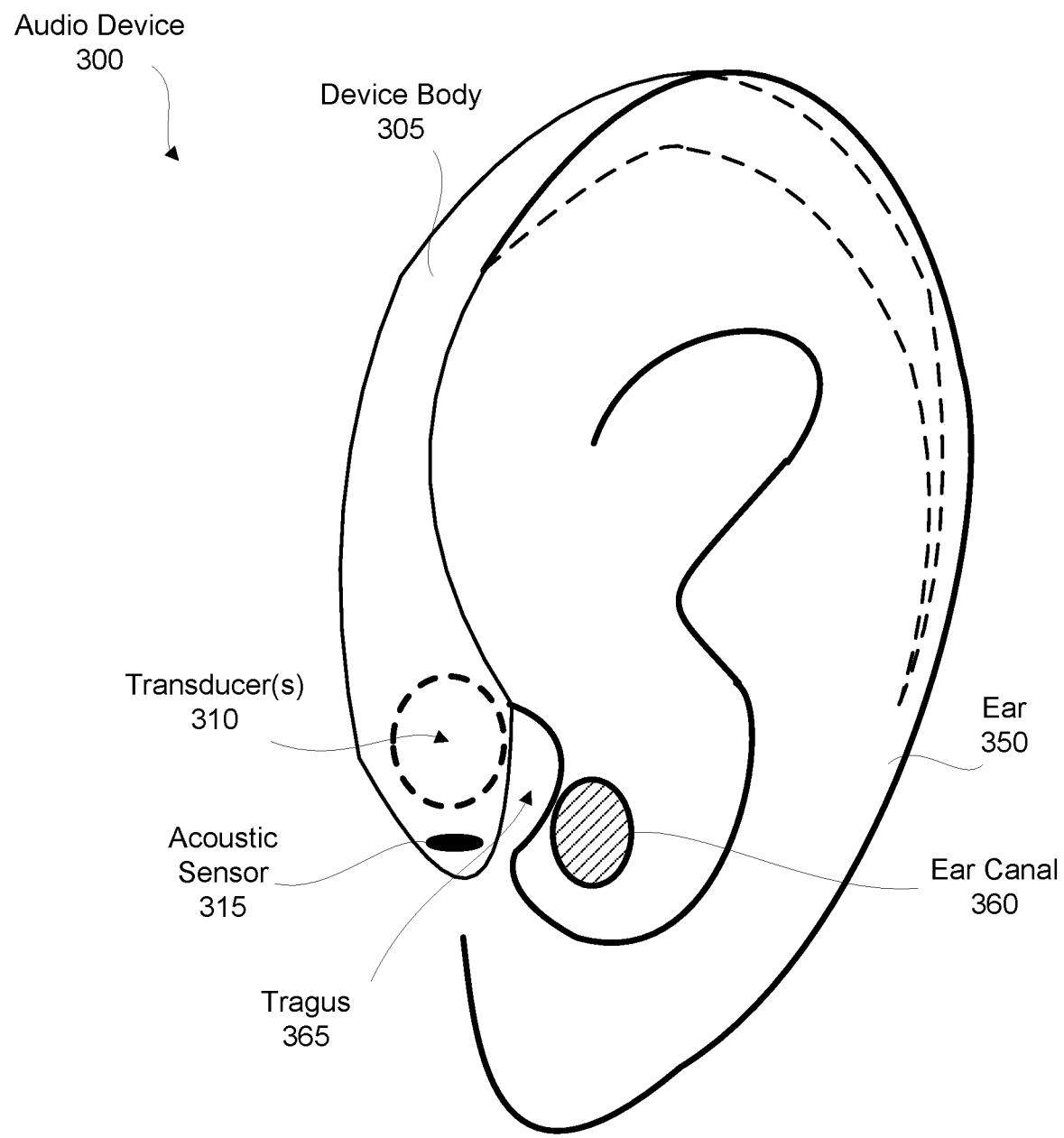
FIG. 3 is an example cartilage conduction audio device including a transducer located on a tragus of the ear of the user, in accordance with an embodiment.

FIG. 3 is another example cartilage conduction audio device 300, in one embodiment. Instead of one or more transducers located along the external rear portion of the ear, the audio device 300 includes a transducer 310 located at a tragus 365 of ear 350. Accordingly, audio device 300 includes a device body 305, the transducer 310 located at the tragus, and an acoustic sensor 315. Similar to the audio device 200, the audio device 300 wraps around the ear 350; however, instead of vibrating the rear external portion of the ear, the transducer 310 vibrates the cartilage of the tragus 365 to produce a sound pressure wave at an entrance of an ear canal 360 of the ear 350. Accordingly, the full 3D geometry of the tragus 365 individualized to that user is used to design and build a custom-made device housing for a tragus conduction transducer that seamlessly conforms to the user's ear and tragus, as shown in FIG. 3. The tragus conduction transducer 310 can be used in conjunction with the one or more transducers 210 behind the ear, as described with respect to FIG. 2.

A Cartilage Conduction Audio Device

Figure 4:
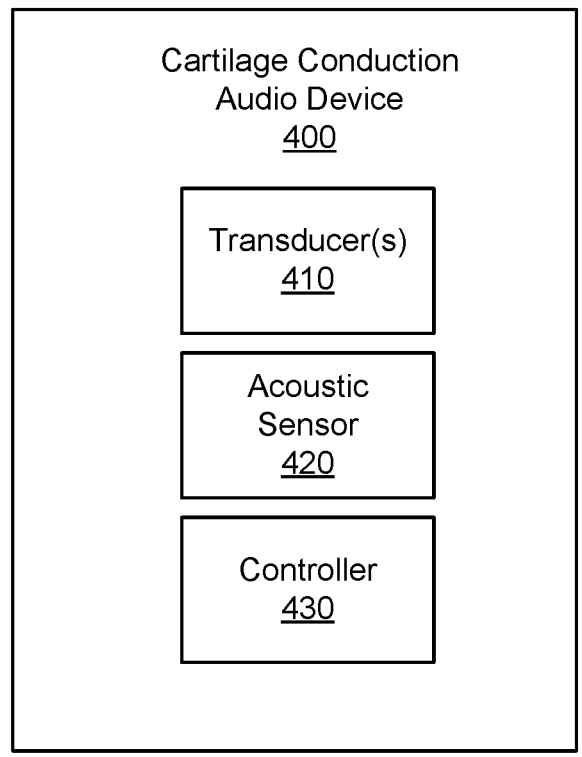
FIG. 4 is a block diagram of a cartilage conduction audio device, in accordance with an embodiment.

FIG. 4 is a block diagram of a cartilage conduction audio device 400 ("audio device 400"), in accordance with an embodiment. The audio device 100 includes one or more transducer(s) 410, an (optional) acoustic sensor 420, and a controller 430.

Each transducer 410 vibrates cartilage of a user's ear in accordance with the vibration instructions (e.g., received from the controller 430). Each transducer 410 is coupled to a first portion of a back of an auricle of an ear of a user and is configured to vibrate the auricle over a frequency range to cause the auricle to create an acoustic pressure wave in accordance with vibration instructions. The transducer may be a single piezoelectric transducer or multiple piezoelectric transducers. A piezoelectric transducer can generate frequencies up to 20 kHz using a range of voltages around +/−100V. The range of voltages may include lower voltages as well (e.g., +/−10V). The piezoelectric transducer may be a stacked piezoelectric actuator. The stacked piezoelectric actuator includes multiple piezoelectric elements that are stacked (e.g. mechanically connected in series). The stacked piezoelectric actuator may have a lower range of voltages because the movement of a stacked piezoelectric actuator can be a product of the movement of a single piezoelectric element with the number of elements in the stack. A piezoelectric transducer is made of a piezoelectric material that can generate a strain (e.g., deformation in the material) in the presence of an electric field. The piezoelectric material may be a polymer (e.g., polyvinyl chloride (PVC), polyvinylidene fluoride (PVDF)), a polymer-based composite, ceramic, or crystal (e.g., quartz (silicon dioxide or $SiO_2$), lead zirconate-titanate (PZT)). By applying an electric field or a voltage across a polymer which is a polarized material, the polymer changes in polarization and may compress or expand depending on the polarity and magnitude of the applied electric field. The piezoelectric transducer may be coupled to a material (e.g., silicone) that attaches well to the back of an ear of a user. In one embodiment, each transducer 410 maintains good surface contact with the back of the user's ear and maintains a steady amount of application force (e.g., 1 Newton) to the user's ear.

In some embodiments, the transducer 410 is configured to generation vibrations over a range of frequencies and includes a first transducer and a second transducer. The first transducer is configured to provide a first portion of the frequency range (e.g., higher range up to 20 kHz). The first transducer may be, e.g., a piezoelectric transducer. The second transducer is configured to provide a second portion of the frequency range (e.g., lower range around 20 Hz). The second transducer may be a piezoelectric transducer or may be a different type of transducer such as a moving coil transducer. A typical moving coil transducer includes a coil of wire and a permanent magnet to produce a permanent magnetic field. Applying a current to the wire while it is placed in the permanent magnetic field produces a force on the coil based on the amplitude and the polarity of the current that can move the coil towards or away from the permanent magnet. The second transducer may be made of a more rigid material than the first transducer. The second transducer may be coupled to a second portion different than the first portion of the back of the ear of the user. Alternatively, the second transducer may be in contact with the skull of the user.

The acoustic sensor 420 provides information regarding the produced sound to the controller 430. The acoustic sensor 420 detects an acoustic pressure wave at an entrance of an ear of a user. In one embodiment, the acoustic sensor 420 is a microphone positioned at an entrance of an ear of a user. A microphone is a transducer that converts pressure into an electrical signal. The frequency response of the microphone may be relatively flat in some portions of a frequency range and may be linear in other portions of a frequency range. The microphone may be configured to receive a gain signal to scale a detected signal from the microphone based on the vibration instructions provided to the transducer 410. For example, the gain may be adjusted based on the vibration instructions to avoid clipping of the detected signal or for improving a signal to noise ratio in the detected signal.

In some embodiments the acoustic sensor 420 may be a vibration sensor. The vibration sensor is coupled to a portion of the ear. In some embodiments, the vibration sensor and the transducer 410 couple to different portions of the ear. The vibration sensor is similar to the transducers used in the transducer except the signal is flowing in reverse. Instead of an electrical signal producing a mechanical vibration in a transducer, a mechanical vibration is generating an electrical signal in the vibration sensor. A vibration sensor may be made of piezoelectric material that can generate an electrical signal when the piezoelectric material is deformed. The piezoelectric material may be a polymer (e.g., PVC, PVDF), a polymer-based composite, ceramic, or crystal (e.g., $SiO_2$, PZT). By applying a pressure on the piezoelectric material, the piezoelectric material changes in polarization and produces an electrical signal. The piezoelectric sensor may be coupled to a material (e.g., silicone) that attaches well to the back of an ear of a user. A vibration sensor can also be an accelerometer. The accelerometer may be piezoelectric or capacitive. A capacitive accelerometer measures changes in capacitance between structures which can be moved by an accelerative force. In one embodiment, the vibration sensor maintains good surface contact with the back of the user's ear and maintains a steady amount of application force (e.g., 1 Newton) to the user's ear. The vibration sensor may be an accelerometer. The vibration sensor may be integrated in an internal measurement unit (IMU) integrated circuit (IC). The IMU is further described with relation to FIG. 6.

The controller 430 controls components of the audio device 400. The controller 430 generates vibration instructions to instruct the transducer 410 how to produce vibrations. For example, vibration instructions may include a content signal (e.g., electrical signal applied to the transducer 410 to produce a vibration), a control signal to enable or disable the transducer 410, and a gain signal to scale the content signal (e.g., increase or decrease the vibrations produced by the transducer 410). The controller 430 generates the content signal of the vibration instructions based on audio content and a frequency response model. A frequency response model describes the response of a system to inputs at certain frequencies and may indicate how an output is shifted in amplitude and phase based on the input. Thus, the controller 430 may generate a content signal (e.g., input signal) of the vibration instructions with the audio content (e.g., target output) and the frequency response model (e.g., relationship of the input to the output). In one embodiment, the controller 430 may generate the content signal of the vibration instructions by applying an inverse of the frequency response to the audio content. The controller 430 receives feedback from an acoustic sensor 420. The acoustic sensor 420 provides information about the sound signal (e.g., acoustic pressure wave) produced by the vibration transducer 410. The controller 430 may compare the detected acoustic pressure wave with a target acoustic pressure wave based on audio content provided to the user. The controller 430 can then compute an inverse function to apply to the detected acoustic wave such that the detected acoustic pressure wave appears the same as the target acoustic pressure wave. Thus, the controller 430 can adjust the frequency response model of the audio device using the computed inverse function specific to each user. The adjustment of the frequency model may be performed while the user is listening to audio content. The controller 430 can then generate updated vibration instructions using the adjusted frequency response model. The controller 430 enables a similar audio experience to be produced across different users of the sound system. In a cartilage conduction audio device, the speaker of the audio device corresponds to a user's auricle. As each auricle of a user is different (e.g., shape and size), the frequency response model will vary from user to user. By adjusting the frequency response model for each user based on audio feedback, the audio device can maintain the same type of produced sound (e.g., neutral listening) regardless of the user. Neutral listening is having similar listening experience across different users. In other words, the listening experience is impartial or neutral to the user (e.g., does not change from user to user).

In one embodiment, the audio device uses a flat spectrum broadband signal to generate the adjusted frequency response model. For example, the controller 430 provides vibration instructions to the transducer 410 based on a flat spectrum broadband signal. The acoustic sensor 420 detects an acoustic pressure wave at an entrance of an ear of the user. The controller 430 compares the detected acoustic pressure wave with the target acoustic pressure wave based on the flat spectrum broadband signal and adjusts the frequency model of the audio device accordingly. In this embodiment, the flat spectrum broadband signal may be used while performing calibration of the audio device for a particular user. Thus, the audio device may perform an initial calibration for a user instead of continuously monitoring the audio device. In this embodiment, the acoustic sensor may be temporarily coupled to the eyewear device for calibration of the user. Responsive to completing calibration of the user, the acoustic sensor may be uncoupled to the eyewear device. Advantages of removing the acoustic sensor from the eyewear device include making it easier to wear and reducing the volume and weight of the eyewear device.

Eyewear Including a Cartilage Conduction Audio Device

Figure 5:
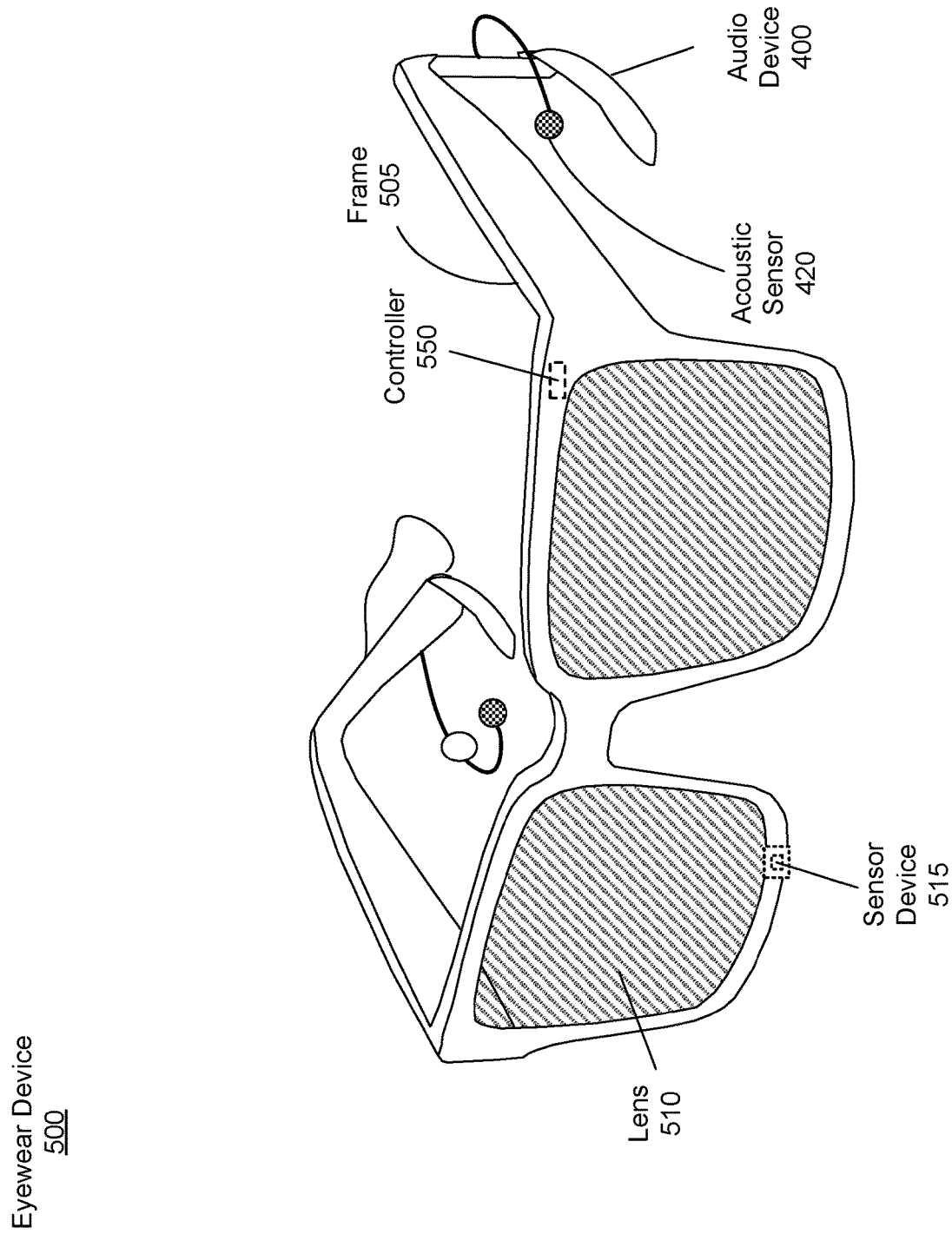
FIG. 5 is an example illustrating an eyewear device including a cartilage conduction audio device, in accordance with an embodiment.

FIG. 5 is an example illustrating a cartilage conduction audio device incorporated into an eyewear device 500, in accordance with an embodiment. The eyewear device 500 presents media to a user. In one embodiment, the eyewear device 500 may be a head mounted display (HMD). Examples of media presented by the eyewear device 500 include one or more images, video, audio, or some combination thereof. The eyewear device 500 may include, among other components, a frame 505, a lens 510, a transducer 410, an acoustic sensor 420, and a controller 430. In some embodiments, the eyewear device 500 may also optionally include a sensor device 515.

The eyewear device 500 may correct or enhance the vision of a user, protect the eye of a user, or provide images to a user. The eyewear device 500 may be eyeglasses which correct for defects in a user's eyesight. The eyewear device 500 may be sunglasses which protect a user's eye from the sun. The eyewear device 500 may be safety glasses which protect a user's eye from impact. The eyewear device 500 may be a night vision device or infrared goggles to enhance a user's vision at night. The eyewear device 500 may be a head mounted display that produces VR, AR, or MR content for the user. Alternatively, the eyewear device 500 may not include a lens 510 and may be a frame 505 with an audio device that provides audio (e.g., music, radio, podcasts) to a user.

The frame 505 includes a front part that holds the lens 510 and end pieces to attach to the user. The front part of the frame 505 bridges the top of a nose of the user. The end pieces (e.g., temples) are portions of the frame 505 to which the temples of a user are attached. The length of the end piece may be adjustable (e.g., adjustable temple length) to fit different users. The end piece may also include a portion that curls behind the ear of the user (e.g., temple tip, ear piece).

The lens 510 provides or transmits light to a user wearing the eyewear device 500. The lens 510 may be prescription lens (e.g., single vision, bifocal and trifocal, or progressive) to help correct for defects in a user's eyesight. The prescription lens transmits ambient light to the user wearing the eyewear device 500. The transmitted ambient light may be altered by the prescription lens to correct for defects in the user's eyesight. The lens 510 may be a polarized lens or a tinted lens to protect the user's eyes from the sun. The lens 510 may be one or more waveguides as part of a waveguide display in which image light is coupled through an end or edge of the waveguide to the eye of the user. The lens 510 may include an electronic display for providing image light and may also include an optics block for magnifying image light from the electronic display. Additional detail regarding the lens 510 can be found in the detailed description of FIG. 6. The lens 510 is held by a front part of the frame 505 of the eyewear device 500.

The sensor device 515 estimates a current position of the eyewear device 500 relative to an initial position of the eyewear device 500. The sensor device 515 may be located on a portion of the frame 505 of the eyewear device 500. The sensor device 515 includes a position sensor and an inertial measurement unit Additional details about the sensor device 515 can be found in the detailed description of FIG. 6.

The audio device of the eyewear device 500 includes the transducer 410, the acoustic sensor 420, and the controller 430. The audio device provides audio content to a user by vibrating the auricle of the ear of the user to produce an acoustic pressure wave. The audio device also uses feedback to create a similar audio experience across different users. Additional detail regarding the audio device can be found in the detailed description of FIG. 4.

The transducer 410 produces sound by vibrating the cartilage in the ear of the user. The transducer 410 is coupled to an end piece of the frame 505 and is configured to be coupled to the back of an auricle of the ear of the user. The auricle is a portion of the outer ear that projects out of a head of the user. The transducer 410 receives vibration instructions from the controller 430. Vibration instructions may include a content signal, a control signal, and a gain signal. The content signal may be based on audio content for presentation to the user. The control signal may be used to enable or disable the transducer 410 or one or more transducers. The gain may be used to amplify the content signal. Two or more transducers may cover different parts of a frequency range. For example, a piezoelectric transducer may be used to cover a first part of a frequency range and a moving coil transducer may be used to cover a second part of a frequency range. Additional detail regarding the transducer 410 can be found in the detailed description of FIG. 4.

The acoustic sensor 420 detects an acoustic pressure wave at an entrance of an ear of a user. The acoustic sensor 420 is coupled to an end piece of the frame 505. The acoustic sensor 420 as shown in FIG. 5 is a microphone which may be positioned at the entrance of the user's ear. In this embodiment, the microphone may directly measure the acoustic pressure wave at the entrance of the ear of the user. Alternatively, the acoustic sensor 420 is a vibration sensor that is configured to be coupled to the back of the pinna of the user. The vibration sensor may indirectly measure the acoustic pressure wave at the entrance of the ear. For example, the vibration sensor may measure a vibration that is a reflection of the acoustic pressure wave at the entrance of the ear and/or measure a vibration created by the transducer on the auricle of the ear of the user which may be used to estimate the acoustic pressure wave at the entrance of the ear. In one embodiment, a mapping between acoustic pressure generated at the entrance to the ear canal and a vibration level generated on the pinna is an experimentally determined quantity that is measured on a representative sample of users and stored. This stored mapping between the acoustic pressure and vibration level (e.g., frequency dependent linear mapping) of the pinna is applied to a measured vibration signal from the vibration sensor which serves as a proxy for the acoustic pressure at the entrance of the ear canal. The vibration sensor can be an accelerometer or a piezoelectric sensor. An accelerometer may be a piezoelectric accelerometer or a capacitive accelerometer. The capacitive accelerometer senses change in capacitance between structures which can be moved by an accelerative force. In some embodiments, the acoustic sensor 420 is removed from the eyewear device 500 after calibration. Additional detail regarding the acoustic sensor 420 can be found in the detailed description of FIG. 4.

The controller 430 provides vibration instructions to the transducer 410, receives information from the acoustic sensor 420 regarding the produced sound, and updates the vibration instructions based on the received information. Vibration instructions instruct the transducer 410 how to produce vibrations. For example, vibration instructions may include a content signal (e.g., electrical signal applied to the transducer 410 to produce a vibration), a control signal to enable or disable the transducer 410, and a gain signal to scale the content signal (e.g., increase or decrease the vibrations produced by the transducer 410). The vibration instructions may be generated by the controller 430. The controller 430 may receive audio content (e.g., music, calibration signal) from a console for presentation to a user and generate vibration instructions based on the received audio content. The controller 430 receives information from the acoustic sensor 420 that describes the produced sound at an ear of the user. In one embodiment the acoustic sensor 420 is a vibration sensor that measures a vibration of a pinna of a user and the controller 430 applies a previously stored frequency dependent linear mapping of pressure to vibration to determine the acoustic pressure wave at the entrance of the ear based on the received detected vibration. The controller 430 uses the received information as feedback to compare the produced sound to a target sound (e.g., audio content) and adjusts the vibration instructions to make the produced sound closer to the target sound. The controller 430 is embedded into the frame 105 of the eyewear device 500. In other embodiments, the controller 430 may be located in a different location. For example, the controller 430 may be part of the transducer or located external to the eyewear device 500. Additional detail regarding the controller 430 can be found in the detailed description of FIG. 3.

System Architecture

Figure 6:
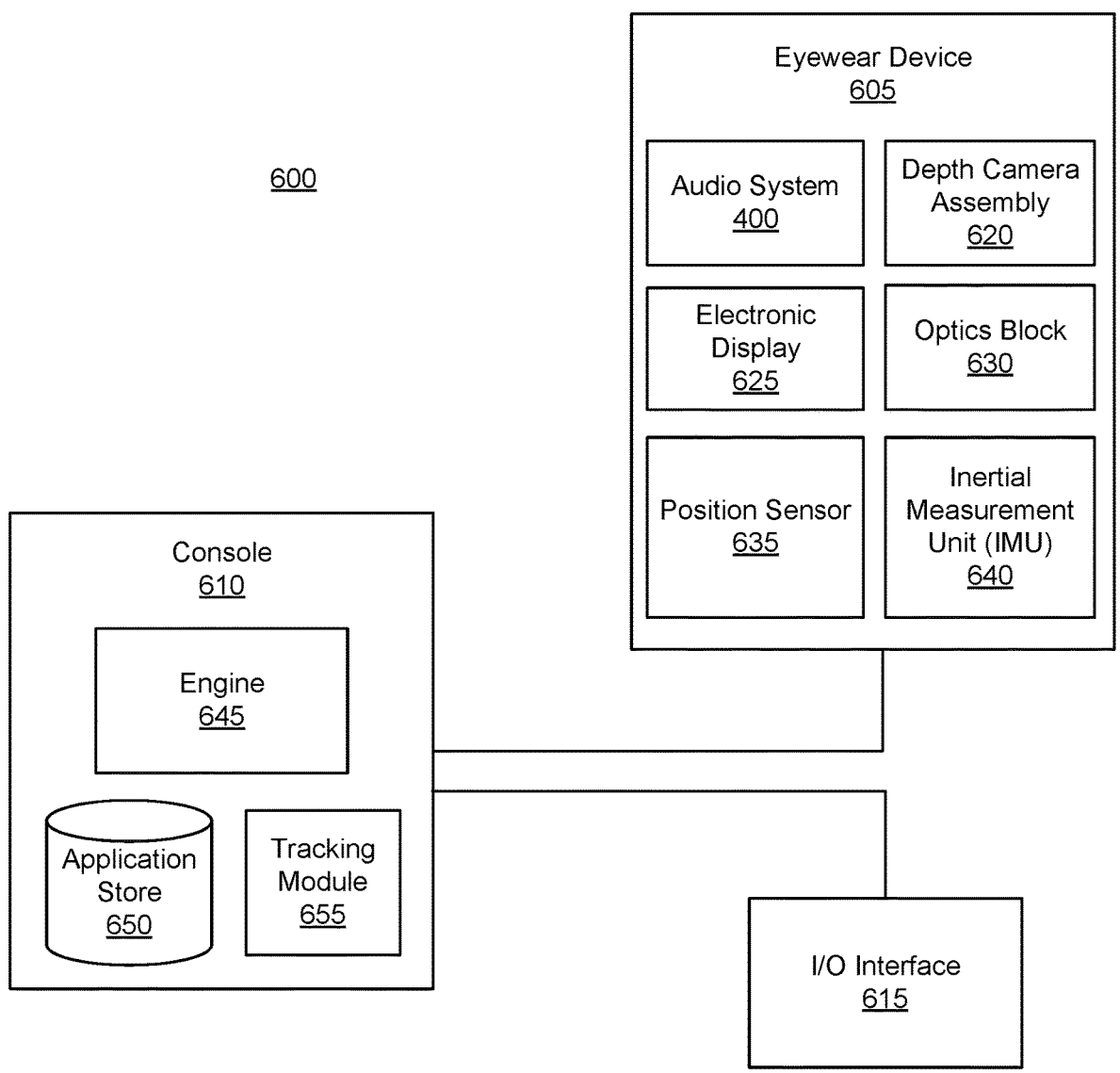
FIG. 6 is a system environment of an eyewear device including a cartilage conduction audio device, in accordance with an embodiment.

FIG. 6 is a system environment 600 of the eyewear device including a cartilage conduction audio device, in accordance with an embodiment. The system 600 may operate in a VR, AR, or MR environment, or some combination thereof. The system 600 shown by FIG. 6 comprises an eyewear device 605 and an input/output (I/O) interface 615 that is coupled to a console 610. The eyewear device 605 may be an embodiment of the eyewear device 600. While FIG. 6 shows an example system 600 including one eyewear device 605 and one I/O interface 615, in other embodiments any number of these components may be included in the system 600. For example, there may be multiple eyewear devices 605 each having an associated I/O interface 615 with each eyewear device 605 and I/O interface 615 communicating with the console 610. In alternative configurations, different and/or additional components may be included in the system 600. Additionally, functionality described in conjunction with one or more of the components shown in FIG. 6 may be distributed among the components in a different manner than described in conjunction with FIG. 6 in some embodiments. For example, some or all of the functionality of the console 610 is provided by the eyewear device 605.

The eyewear device 605 may be a head-mounted display that presents content to a user comprising augmented views of a physical, real-world environment with computer-generated elements (e.g., two dimensional (2D) or three dimensional (3D) images, 2D or 3D video, sound, etc.). In some embodiments, the presented content includes audio that is presented via an audio block 620 that receives audio information from the eyewear device 605, the console 610, or both, and presents audio data based on the audio information. The eyewear device 605 may comprise one or more rigid bodies, which may be rigidly or non-rigidly coupled to each other together. A rigid coupling between rigid bodies causes the coupled rigid bodies to act as a single rigid entity. In contrast, a non-rigid coupling between rigid bodies allows the rigid bodies to move relative to each other. In some embodiments, the eyewear device 605 presents virtual content to the user that is based in part on a real environment surrounding the user. For example, virtual content may be presented to a user of the eyewear device. The user physically may be in a room, and virtual walls and a virtual floor of the room are rendered as part of the virtual content.

The eyewear device 605 includes an audio block 620. The audio block 620 is one embodiment of the audio device 300. The audio block 620 is a cartilage conduction audio device which provides audio information to a user by vibrating the cartilage in a user's ear to produce sound. The audio block 620 monitors the produced sound so that it can compensate for a frequency response model for each ear of the user and can maintain the same type of produced sound across different individuals.

The eyewear device 605 may include an electronic display 625, an optics block 630, one or more position sensors 635, and an inertial measurement Unit (IMU) 640. The electronic display 625 and the optics block 630 is one embodiment of a lens 610. The position sensors 635 and the IMU 640 is one embodiment of sensor device 615. Some embodiments of the eyewear device 605 have different components than those described in conjunction with FIG. 6. Additionally, the functionality provided by various components described in conjunction with FIG. 6 may be differently distributed among the components of the eyewear device 605 in other embodiments, or be captured in separate assemblies remote from the eyewear device 605.

The electronic display 625 displays 2D or 3D images to the user in accordance with data received from the console 610. In various embodiments, the electronic display 625 comprises a single electronic display or multiple electronic displays (e.g., a display for each eye of a user). Examples of the electronic display 625 include: a liquid crystal display (LCD), an organic light emitting diode (OLED) display, an active-matrix organic light-emitting diode display (AMOLED), some other display, or some combination thereof.

The optics block 630 magnifies image light received from the electronic display 625, corrects optical errors associated with the image light, and presents the corrected image light to a user of the eyewear device 605. In various embodiments, the optics block 630 includes one or more optical elements. Example optical elements included in the optics block 630 include: an aperture, a Fresnel lens, a convex lens, a concave lens, a filter, a reflecting surface, or any other suitable optical element that affects image light. Moreover, the optics block 630 may include combinations of different optical elements. In some embodiments, one or more of the optical elements in the optics block 630 may have one or more coatings, such as partially reflective or anti-reflective coatings.

Magnification and focusing of the image light by the optics block 630 allows the electronic display 625 to be physically smaller, weigh less, and consume less power than larger displays. Additionally, magnification may increase the field of view of the content presented by the electronic display 625. For example, the field of view of the displayed content is such that the displayed content is presented using almost all (e.g., approximately 110 degrees diagonal), and in some cases all, of the user's field of view. Additionally in some embodiments, the amount of magnification may be adjusted by adding or removing optical elements.

In some embodiments, the optics block 630 may be designed to correct one or more types of optical error. Examples of optical error include barrel or pincushion distortion, longitudinal chromatic aberrations, or transverse chromatic aberrations. Other types of optical errors may further include spherical aberrations, chromatic aberrations, or errors due to the lens field curvature, astigmatisms, or any other type of optical error. In some embodiments, content provided to the electronic display 625 for display is pre-distorted, and the optics block 630 corrects the distortion when it receives image light from the electronic display 625 generated based on the content.

The IMU 640 is an electronic device that generates data indicating a position of the eyewear device 605 based on measurement signals received from one or more of the position sensors 635. A position sensor 635 generates one or more measurement signals in response to motion of the eyewear device 605. Examples of position sensors 635 include: one or more accelerometers, one or more gyroscopes, one or more magnetometers, another suitable type of sensor that detects motion, a type of sensor used for error correction of the IMU 640, or some combination thereof. The position sensors 635 may be located external to the IMU 640, internal to the IMU 640, or some combination thereof.

Based on the one or more measurement signals from one or more position sensors 635, the IMU 640 generates data indicating an estimated current position of the eyewear device 605 relative to an initial position of the eyewear device 605. For example, the position sensors 635 include multiple accelerometers to measure translational motion (forward/back, up/down, left/right) and multiple gyroscopes to measure rotational motion (e.g., pitch, yaw, and roll). In some embodiments, the IMU 640 rapidly samples the measurement signals and calculates the estimated current position of the eyewear device 605 from the sampled data. For example, the IMU 640 integrates the measurement signals received from the accelerometers over time to estimate a velocity vector and integrates the velocity vector over time to determine an estimated current position of a reference point on the eyewear device 605. Alternatively, the IMU 640 provides the sampled measurement signals to the console 610, which interprets the data to reduce error. The reference point is a point that may be used to describe the position of the eyewear device 605. The reference point may generally be defined as a point in space or a position related to the eyewear device's 605 orientation and position.

The IMU 640 receives one or more parameters from the console 610. As further discussed below, the one or more parameters are used to maintain tracking of the eyewear device 605. Based on a received parameter, the IMU 640 may adjust one or more IMU parameters (e.g., sample rate). In some embodiments, certain parameters cause the IMU 640 to update an initial position of the reference point so it corresponds to a next position of the reference point. Updating the initial position of the reference point as the next calibrated position of the reference point helps reduce accumulated error associated with the current position estimated the IMU 640. The accumulated error, also referred to as drift error, causes the estimated position of the reference point to "drift" away from the actual position of the reference point over time. In some embodiments of the eyewear device 605, the IMU 640 may be a dedicated hardware component. In other embodiments, the IMU 640 may be a software component implemented in one or more processors.

The I/O interface 615 is a device that allows a user to send action requests and receive responses from the console 610. An action request is a request to perform a particular action. For example, an action request may be an instruction to start or end capture of image or video data, or an instruction to perform a particular action within an application. The I/O interface 615 may include one or more input devices. Example input devices include: a keyboard, a mouse, a game controller, or any other suitable device for receiving action requests and communicating the action requests to the console 610. An action request received by the I/O interface 615 is communicated to the console 610, which performs an action corresponding to the action request. In some embodiments, the I/O interface 615 includes an IMU 640, as further described above, that captures calibration data indicating an estimated position of the I/O interface 615 relative to an initial position of the I/O interface 615. In some embodiments, the I/O interface 615 may provide haptic feedback to the user in accordance with instructions received from the console 610. For example, haptic feedback is provided when an action request is received, or the console 610 communicates instructions to the I/O interface 615 causing the I/O interface 615 to generate haptic feedback when the console 610 performs an action.

The console 610 provides content to the eyewear device 605 for processing in accordance with information received from one or more of: the eyewear device 605 and the I/O interface 615. In the example shown in FIG. 6, the console 610 includes an application store 650, a tracking module 655 and an engine 645. Some embodiments of the console 610 have different modules or components than those described in conjunction with FIG. 6. Similarly, the functions further described below may be distributed among components of the console 610 in a different manner than described in conjunction with FIG. 6.

The application store 650 stores one or more applications for execution by the console 610. An application is a group of instructions, that when executed by a processor, generates content for presentation to the user. Content generated by an application may be in response to inputs received from the user via movement of the eyewear device 605 or the I/O interface 615. Examples of applications include: gaming applications, conferencing applications, video playback applications, or other suitable applications.

The tracking module 655 calibrates the system environment 600 using one or more calibration parameters and may adjust one or more calibration parameters to reduce error in determination of the position of the eyewear device 605 or of the I/O interface 615. Calibration performed by the tracking module 655 also accounts for information received from the IMU 640 in the eyewear device 605 and/or an IMU 640 included in the I/O interface 615. Additionally, if tracking of the eyewear device 605 is lost, the tracking module 655 may re-calibrate some or all of the system environment 600.

The tracking module 655 tracks movements of the eyewear device 605 or of the I/O interface 615 using information from the one or more position sensors 635, the IMU 640 or some combination thereof. For example, the tracking module 655 determines a position of a reference point of the eyewear device 605 in a mapping of a local area based on information from the eyewear device 605. The tracking module 655 may also determine positions of the reference point of the eyewear device 605 or a reference point of the I/O interface 615 using data indicating a position of the eyewear device 605 from the IMU 640 or using data indicating a position of the I/O interface 615 from an IMU 640 included in the I/O interface 615, respectively. Additionally, in some embodiments, the tracking module 655 may use portions of data indicating a position or the eyewear device 605 from the IMU 640 to predict a future location of the eyewear device 605. The tracking module 655 provides the estimated or predicted future position of the eyewear device 605 or the I/O interface 615 to the engine 645.

The engine 645 also executes applications within the system environment 600 and receives position information, acceleration information, velocity information, predicted future positions, or some combination thereof, of the eyewear device 605 from the tracking module 655. Based on the received information, the engine 645 determines content to provide to the eyewear device 605 for presentation to the user. For example, if the received information indicates that the user has looked to the left, the engine 645 generates content for the eyewear device 605 that mirrors the user's movement in a virtual environment or in an environment augmenting the local area with additional content. Additionally, the engine 645 performs an action within an application executing on the console 610 in response to an action request received from the I/O interface 615 and provides feedback to the user that the action was performed. The provided feedback may be visual or audible feedback via the eyewear device 605 or haptic feedback via the I/O interface 615.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A method comprising:
receiving data for a shape of an ear of a user, the shape including an external portion of the ear; and
applying a model to the data for the shape of the ear of the user, the model identifying one or more locations for one or more transducers of a cartilage conduction audio device along a surface of the external portion of the ear such that the one or more locations of the one or more transducers do not block an entrance of an ear canal of the user, the one or more locations for the one or more transducers resulting in a pressure wave maxima at the entrance of the ear canal of the user, each of the one or more transducers configured to vibrate the external portion of the ear to create the acoustic pressure wave.

2. The method of claim 1, wherein the model varies a location of each of the one or more transducers along the surface of the external portion of the ear to determine the pressure wave maxima at the entrance of the ear canal of the user.

3. The method of claim 1, further comprising:
generating a design for the cartilage conduction audio device using the one or more identified locations for the user, the cartilage conduction audio device including a body configured to substantially conform to the surface of the external portion of the ear, wherein the design is used to fabricate the cartilage conduction audio device.

4. The method of claim 1, wherein the body of the cartilage conduction audio device is a molded plastic and the one or more transducers reside in the body of the cartilage conduction audio device.

5. The method of claim 1, wherein each of the one or more transducers are configured to vibrate the external portion of the ear over a frequency range to cause the external portion of the ear to create the acoustic pressure wave that propagates towards the entrance of the ear of the user without occluding the entrance.

6. The method of claim 1, wherein the data describing the shape of the ear of the user is generated using a custom impression of an outside of the ear for the user.

7. The method of claim 6, wherein a Silicone based material with a shore-A hardness is used to make the custom impression of an outside of the ear for the user.

8. The method of claim 1, wherein the data describing the shape of the ear of the user is generated using a three-dimensional reconstruction process that captures images of the ear of the user.

9. The method of claim 1, wherein the external portion of the ear comprises a back of an auricle of the ear, and wherein the one or more transducers a placed substantially flush against the auricle of the ear when worn by the user.

10. The method of claim 9, wherein the shape of the ear further includes a tragus of the ear.

11. The method of claim 1, wherein the one or more locations for the one or more transducers correspond to an arrangement of the one or more transducers along the external portion of the ear of the user that produces an acoustic pressure wave maximum from individual acoustic pressure waves of each of the one or more transducers, the arrangement of the one or more transducers being limited by a geometry of the ear of the user.

12. The method of claim 1, wherein a transducer of the one or more transducers is a transducer selected from a group consisting of: a piezoelectric transducer and a voice coil transducer.

13. A method comprising:
receiving data describing a shape of an ear of a user for use in generating a cartilage conduction audio device, the shape including an external portion of the ear;
applying a model to the data for the shape of the ear of the user, the model identifying one or more locations for one or more transducers of a cartilage conduction audio device along a surface of the external portion of the ear such that the one or more locations of the one or more transducers do not block an entrance of an ear canal of the user, the one or more locations for the one or more transducers resulting in a pressure wave maxima at the entrance of the ear canal of the user, each of the one or more transducers configured to vibrate the external portion of the ear to create the acoustic pressure wave;
generating a design for the cartilage conduction audio device using the one or more identified locations for the user, the cartilage conduction audio device including a body configured to substantially conform to the surface of the external portion of the ear; and
fabricating the cartilage conduction audio device including providing a transducer of the one or more transducers in the device body corresponding to the location for each transducer at each of the one or more identified locations, wherein the one or more transducers are coupled to a controller.

14. The method of claim 13, wherein the model varies a location of each of the one or more transducers along the surface of the external portion of the ear to determine the pressure wave maxima at the entrance of the ear canal of the user.

15. The method of claim 13, wherein the controller is configured to:
receive acoustic pressure wave feedback generated by the one or more transducers of the cartilage conduction audio device;
dynamically adjust a frequency response model based on the acoustic pressure wave feedback; and
update the vibration instructions using the adjusted frequency response model.

16. The method of claim 13, wherein the acoustic pressure wave feedback is received from an acoustic sensor located adjacent a location corresponding to the entrance of the ear.

17. The method of claim 13, wherein an acoustic sensor is incorporated in the device body of the cartilage conduction audio device and configured to provide real-time sound pressure wave feedback and operate as a microphone for voice recognition phone call communications.

18. The method of claim 13, further comprising:
incorporating the cartilage conduction audio device into at least one of an augmented reality eyewear device or a virtual reality eyewear device configured to present content to a user via a display screen presented within the eyewear device.

19. The method of claim 13, wherein each of the one or more transducers are configured to vibrate the external portion of the ear over a frequency range to cause the external portion of the ear to create the acoustic pressure wave that propagates towards the entrance of the ear of the user without occluding the entrance.

20. The method of claim 13, wherein the data describing the shape of the ear of the user is generated using a custom impression of an outside of the ear for the user, and wherein a Silicone based material with a shore-A hardness is used to make the custom impression of an outside of the ear for the user.

* * * * *